US012070477B2

(12) United States Patent
Ko et al.

(10) Patent No.: US 12,070,477 B2
(45) Date of Patent: Aug. 27, 2024

(54) LACTOBACILLUS SP. STRAIN HAVING ABILITY TO INHIBIT GROWTH OF VAGINAL PATHOGENIC MICROORGANISMS

(71) Applicant: KoBioLabs, Inc., Seoul (KR)

(72) Inventors: Gwang Pyo Ko, Seoul (KR); Hyun Ju You, Incheon (KR); Bo Mi Kwon, Seoul (KR)

(73) Assignee: KOBIOLABS, INC., Seoul (KR)

( * ) Notice: Subject to any disclaimer, the term of this patent is extended or adjusted under 35 U.S.C. 154(b) by 186 days.

(21) Appl. No.: 17/019,677

(22) Filed: Sep. 14, 2020

(65) Prior Publication Data
US 2020/0405789 A1     Dec. 31, 2020

Related U.S. Application Data

(63) Continuation of application No. 15/566,352, filed as application No. PCT/KR2016/002988 on Mar. 24, 2016, now abandoned.

(30) Foreign Application Priority Data

Apr. 16, 2015   (KR) .................. 10-2015-0053702
Feb. 25, 2016   (KR) .................. 10-2016-0022840

(51) Int. Cl.
| | | |
|---|---|---|
| A61K 35/747 | (2015.01) |
| A23C 9/123 | (2006.01) |
| A23L 2/52 | (2006.01) |
| A23L 33/00 | (2016.01) |
| A23L 33/135 | (2016.01) |
| A61P 15/02 | (2006.01) |
| A61P 31/04 | (2006.01) |
| A61P 31/10 | (2006.01) |
| A61P 31/20 | (2006.01) |
| C12N 1/20 | (2006.01) |
| C12R 1/225 | (2006.01) |

(52) U.S. Cl.
CPC .......... *A61K 35/747* (2013.01); *A23C 9/1234* (2013.01); *A23L 33/135* (2016.08); *A23L 33/40* (2016.08); *A61P 15/02* (2018.01); *A61P 31/04* (2018.01); *A61P 31/10* (2018.01); *A61P 31/20* (2018.01); *C12N 1/205* (2021.05); *A23L 2/52* (2013.01); *A23V 2002/00* (2013.01); *A23V 2400/11* (2023.08); *A23V 2400/143* (2023.08); *A23V 2400/145* (2023.08); *A23V 2400/149* (2023.08); *C12R 2001/225* (2021.05)

(58) Field of Classification Search
CPC ..... A61K 35/747; A23L 33/135; A61P 15/02; A61P 31/04; A61P 31/10; A61P 31/20; A23Y 2220/35; A23Y 2220/37; A23Y 2220/41; C12R 2001/225
See application file for complete search history.

(56) References Cited

U.S. PATENT DOCUMENTS

| | | |
|---|---|---|
| 2011/0151462 A1 | 6/2011 | Tynan |
| 2013/0171253 A1 | 7/2013 | Kiss et al. |
| 2014/0147425 A1 | 5/2014 | Henn et al. |

FOREIGN PATENT DOCUMENTS

| | | |
|---|---|---|
| EP | 1424075 | 6/2004 |
| KR | 10-1999-0083612 | 11/1999 |
| KR | 10-2011-0117386 | 10/2011 |
| KR | 10-2013-0049056 | 5/2013 |

OTHER PUBLICATIONS

Z. Ling et al., "The Restoration of the Vaginal Microbiota After Treatment for Bacterial Vaginosis with Metronidazole or Probiotics", Microbial Ecology, vol. 65, No. 3, p. 773-780, 2013.
P. Mastromarino et al., "Bacterial vaginosis: a review on clinical trials with probiotics", New Microbiologica, vol. 36, No. 3, p. 229-238, 2013.
M. N. Matu et al., "In vitro inhibitory activity of human vaginal lactobacilli against pathogenic bacteria associated with bacterial vaginosis in Kenyan women", Anaerobe, vol. 16, p. 210-215, 2010, Elsevier.
F. Atassi et al, "Lactobacilus strains isolated from the vaginal microbiota of healthy women inhibit Prevotella bivia and Gardnerella vaginalis in coculture and cell culture", FEMS Immunol Med Microbiol, vol. 48, p. 424-432, 2006.
B.M. Ngugi et al., "Effects of BV-Associated Bacteria and Sexual Intercourse on Vaginal Colonization with the Probiotic Lactobacillus crispatus CTV-05", Sexually Transmitted Diseases, vol. 38, No. 11, p. 1020-1027, Nov. 2011.
H. S. Kim et al., "Antioxidative and Probiotic Properties of Lactobacillus gasseri NLRI-312 Isolated from Korean Infant Feces", Asian-Aust. J. Anim. Sci., vol. 19, No. 9: 1335-1341, Sep. 2006.

*Primary Examiner* — Louise W Humphrey
*Assistant Examiner* — Alexander M Duryee
(74) *Attorney, Agent, or Firm* — LEX IP MEISTER, PLLC

(57) ABSTRACT

The present invention relates to a novel *Lactobacillus* sp. isolation strain having an activity to inhibit the growth of vaginitis pathogens, and a pharmaceutical composition, a health functional food, and a cleansing product, comprising the strain as an active ingredient. Therefore, the present invention exhibits an effect of inhibiting the growth of *Sneathia* spp. pathogens associated with the infection with human papillomavirus (HPV) and the incidence of bacterial vaginitis, *Gardnerella vaginalis* as a vaginitis pathogen, and *Candida albicans* as a causative yeast of *Candidal vaginitis*, and an effect of recovering and maintaining the vaginal microflora, and thus can be used for the prevention and treatment of female vaginitis.

5 Claims, 5 Drawing Sheets
Specification includes a Sequence Listing.

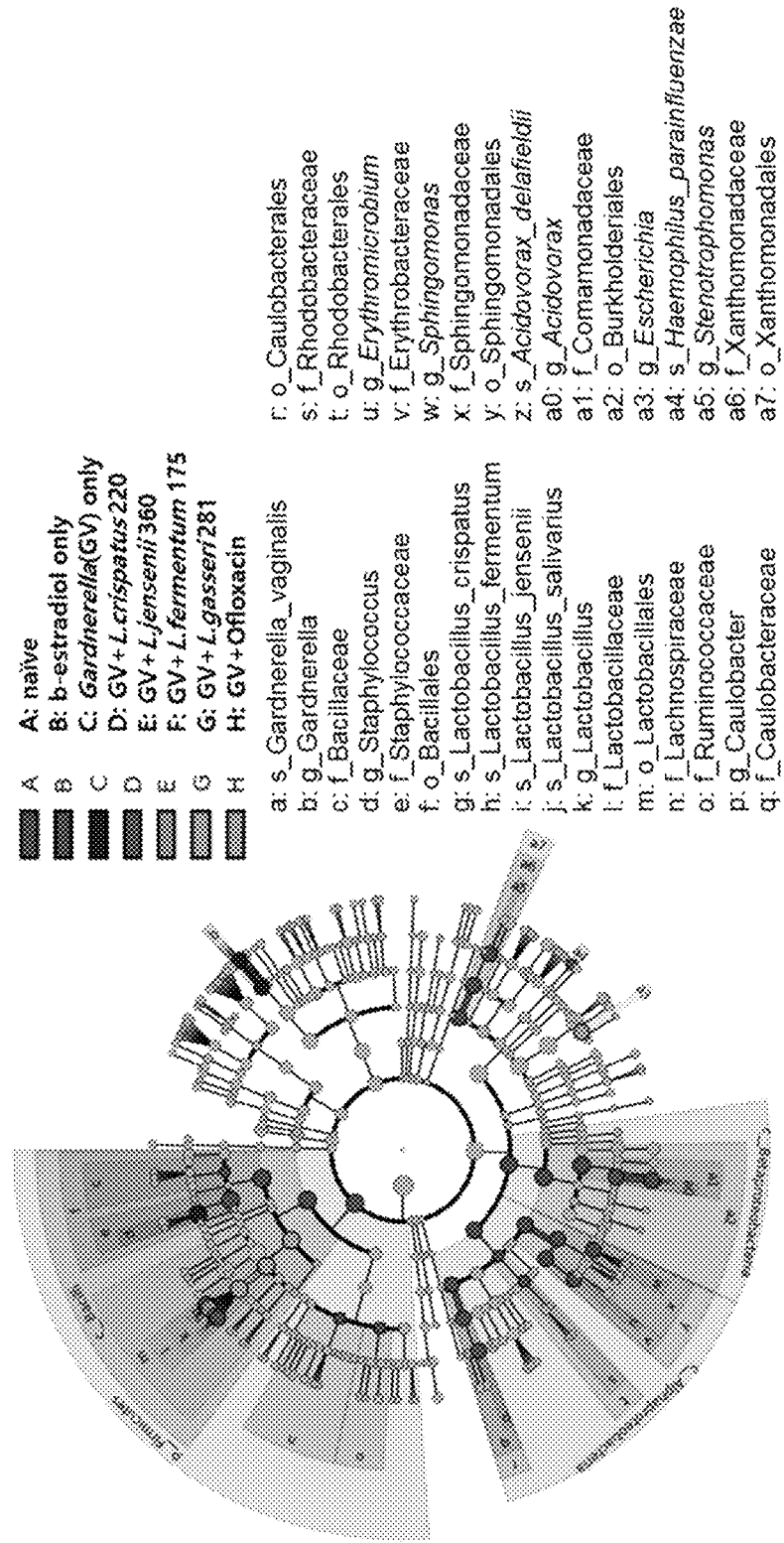

SEQUENCE LISTING

```
<160> NUMBER OF SEQ ID NOS: 6

<210> SEQ ID NO 1
<211> LENGTH: 944
<212> TYPE: DNA
<213> ORGANISM: Lactobacillus crispatus

<400> SEQUENCE: 1
ttacttcggc aatgacgtta ggaaagcgag cggcggatgg gtgagtaaca cgtggggaac      60
ctgccccata gtctgggata ccacttggaa acaggtgcta ataccggata agaaagcaga     120
tcgcatgatc agcttttaaa aggcggcgta agctgtcgct atgggatggc cccgcggtgc     180
attagctagt tggtaaggta aaggcttacc aaggcgatga tgcatagccg agttgagaga     240
ctgatcggcc acattgggac tgagacacgg cccaaactcc tacgggaggc agcagtaggg     300
aatcttccac aatggacgca agtctgatgg agcaacgccg cgtgagtgaa gaaggttttc     360
ggatcgtaaa gctctgttgt tggtgaagaa ggatagaggt agtaactggc ctttatttga     420
cggtaatcaa ccagaaagtc acggctaact acgtgccagc agccgcggta atacgtaggt     480
ggcaagcgtt gtccggattt attgggcgta aagcgagcgc aggcggaaga ataagtctga     540
tgtgaaagcc ctcggcttaa ccgaggaact gcatcggaaa ctgttttct tgagtgcaga     600 agaggagagt ggaactccat gtgtagcggt ggaatgcgta gatatatgga agaacaccag     660
tggcgaaggc ggctctctgg tctgcaactg acgctgaggc tcgaaagcat gggtagcgaa     720
caggattaga tacctggta gtccatgccg taaacgatga gtgctaagtg ttgggaggtt     780
tccgcctctc agtgctgcag ctaacgcatt aagcactccg cctggggagt acgaccgcaa     840
ggttgaaact caaaggaatt gacggggggcc cgcacaagcg gtggagcatg tggtttaatt     900
cgaagcaacg cgaagaacct taccaggtct tgacatctag tgcc                      944

<210> SEQ ID NO 2
<211> LENGTH: 715
<212> TYPE: DNA
<213> ORGANISM: Lactobacillus fermentum

<400> SEQUENCE: 2
ctgcccagaa gcgggggaca catttggaa acagatgcta ataccgcata acaacgttgt       60
```

```
tcgcatgaac aacgcttaaa agatggcttc tcgctatcac ttctggatgg acctgcggtg    120
cattagcttg ttggtggggt aacggcctac caaggcgatg atgcatagcc gagttgagag    180
actgatcggc cacaatggga ctgagacacg gcccatactc ctacgggagg cagcagtagg    240
gaatcttcca caatgggcgc aagcctgatg agcaacacc gcgtgagtga agaagggttt     300
cggctcgtaa agctctgttg ttaaagaaga acacgtatga gagtaactgt tcatacgttg    360
acggtattta accagaaagt cacggctaac tacgtgccag cagccgcggt aatacgtagg    420
tggcaagcgt tatccggatt tattgggcgt aaagagagtg caggcggttt tctaagtctg    480
atgtgaaagc cttcggctta accggagaag tgcatcggaa actggataac ttgagtgcag    540
aagagggtag tggaactcca tgtgtagcgg tggaatgcgt agatatatgg aagaacacca    600
gtggcgaagg cggctacctg gtctgcaact gacgctgaga ctcgaaagca tgggtagcga    660
acaggattag ataccctggt agtccatgcc gtaaacgatg agtgctaggt gttgg         715

<210> SEQ ID NO 3
<211> LENGTH: 718
<212> TYPE: DNA
<213> ORGANISM: Lactobacillus jensenii

<400> SEQUENCE: 3
aaaagctact ttcgcatgaa agaagtttaa aaggcggcgt aagctgtcgc taaaggatgg     60
acctgcgatg cattagctag ttggtaaggt aacggcttac caaggcgatg atgcatagcc    120
gagttgagag actgatcggc cacattggga ctgagacacg gcccaaactc ctacgggagg    180
cagcagtagg gaatcttcca caatggacga aagtctgatg agcaacgcc gcgtgagtga     240 agaaggtttt cggatcgtaa agctctgttg ttggtgaaga aggatagagg tagtaactgg    300
cctttatttg acggtaatca accagaaagt cacggctaac tacgtgccag cagccgcggt    360
aatacgtagg tggcaagcgt tgtccggatt tattgggcgt aaagcgagcg caggcggatt    420
gataagtctg atgtgaaagc cttcggctca accgaagaac tgcatcagaa actgtcaatc    480
ttgagtgcag aagaggagag tggaactcca tgtgtagcgg tggaatgcgt agatatatgg    540
aagaacacca gtggcgaagg cggctctctg gtctgtaact gacgctgagg ctcgaaagca    600
tgggtagcga acaggattag ataccctggt agtccatgcc gtaaacgatg agtgctaagt    660
gttgggaggt ttccgcctct cagtgctgca gctaacgcat taagcactcc gcctgggg     718

<210> SEQ ID NO 4
<211> LENGTH: 722
<212> TYPE: DNA
<213> ORGANISM: Lactobacillus gasseri

<400> SEQUENCE: 4
cggataacaa cactagacgc atgtctagag tttaaaagat ggttctgcta tcactcttgg     60
atggacctgc ggtgcattag ctagttggta aggcaacggc ttaccaaggc aatgatgcat    120
agccgagttg agagactgat cggccacatt gggactgaga cacggcccaa actcctacgg    180
gaggcagcag tagggaatct tccacaatgg acgcaagtct gatggagcaa cgccgcgtga    240
gtgaagaagg gtttcggctc gtaaagctct gttggtagta agaaagata gaggtagtaa    300 ctggccttta tttgacggta attacttaga aagtcacggc taactacgtg ccagcagccg    360
cggtaatacg taggtggcaa gcgttgtccg gatttattgg gcgtaaagcg agtgcaggcg    420
gttcaataag tctgatgtga aagccttcgg ctcaaccgga gaattgcatc agaaactgtt    480
```

```
                                              -continued gaacttgagt  gcagaagagg  agagtggaac  tccatgtgta  gcggtggaat  gcgtagatat    540
atggaagaac  accagtggcg  aaggcggctc  tctggtctgc  aactgacgct  gaggctcgaa    600
agcatgggta  gcgaacagga  ttagataccc  tggtagtcca  tgccgtaaac  gatgagtgct    660
aagtgttggg  aggtttccgc  ctctcagtgc  tgcagctaac  gcattaagca  ctccgcctgg    720
gg                                                                        722

<210> SEQ ID NO 5
<211> LENGTH: 20
<212> TYPE: DNA
<213> ORGANISM: Artificial Sequence
<220> FEATURE:
<223> OTHER INFORMATION: UnivFwd primer

<400> SEQUENCE: 5
agagtttgat cmtggctcag                                                      20

<210> SEQ ID NO 6
<211> LENGTH: 19
<212> TYPE: DNA
<213> ORGANISM: Artificial Sequence
<220> FEATURE:
<223> OTHER INFORMATION: UnivRev primer

<400> SEQUENCE: 6
ggytaccttg ttacgactt                                                       19
```

LACTOBACILLUS SP. STRAIN HAVING ABILITY TO INHIBIT GROWTH OF VAGINAL PATHOGENIC MICROORGANISMS

CROSS-REFERENCE TO RELATED APPLICATIONS

This application is a Continuation Application of U.S. patent application Ser. No. 15/566,352, which was filed on Oct. 13, 2017, which claims the benefit of Korean Patent Application Nos. 10-2015-0053702 on Apr. 16, 2015 and 10-2016-0022840 on Feb. 25, 2016 with the Korean Intellectual Property Office, the disclosure of which is herein incorporated by reference in its entirety.

TECHNICAL FIELD

The present invention activity relates to a *Lactobacillus* sp. strain having an ability to inhibit the growth of pathogenic vaginal microorganisms, a growth inhibitor of pathogenic vaginal microorganisms including the same as an active ingredient, and a product for improving, preventing or treating vaginitis including the inhibitor. More specifically, the present invention relates to a novel *Lactobacillus* sp. strain having an inhibitory effect on the growth of pathogenic vaginal microorganisms wherein the pathogenic vaginal microorganisms include fungi, bacteria and viruses, and specific examples thereof include *Candidia* spp. strains, *Gardnerella* spp. strains, or *Sneathia* spp. strains, or the like, and a pharmaceutical composition, a health functional food or a cleansing product including the same as an active ingredient.

BACKGROUND ART

Globally, three-quarters of the female population is experiencing an infection of inflammatory diseases of the female genitalia including bacterial vaginitis during a period of their life, and it has been reported that 50% of them experience recurrence. In addition, more than 60% of female vaginitis corresponds to asymptomatic infections, and susceptibility to vaginitis is greatly increased through antibiotics, stress, hormonal changes after menopause, and the like.

There are three types and causes of vaginitis caused by infection, including bacterial vaginosis (BV), *candida* vaginitis (CV) and *trichomonas* vulvovaginitis. Among them, the bacterial vaginosis has been recognized as the most common vaginitis, and it has been reported that *Atopobium vaginae, Megasphaera* sp., *Gardnerella vaginalis, Eggerthella* sp., *Clostridium*-like sp., *Prevotella bivia, Peptostreptococcus micros*, or the like have been found in the vaginal secretions isolated from patients with bacterial vaginosis. In particular, *Gardnerella vaginalis* is known as the major causative bacteria of bacterial vaginosis.

Microbial communities in women's vagina are the major factor for maintaining vaginal health, and various bacteria, yeast and other microorganisms coexist in balance. The dominant species of healthy vaginal microflora is lactate-producing *Lactobacillus* sp., and it is known to inhibit various pathogens causing female diseases including vaginitis by performing functions, such as maintaining vaginal acidity, producing hydrogen peroxide and activating mucosal immune system, and the like.

Conventional treatment of vaginitis using antibiotics is accompanied by various side effects, such as an increase in recurrence rate, a decrease in abundance of *Lactobacillus* spp., the generation of inflammation caused by other antibiotic resistant strains besides *Gardnerella* sp. and *Candida* sp. Therefore, the importance of inhibiting growth of vaginitis pathogens and recovering vaginal microflora using probiotic *Lactobacillus* spp. has been highlighted.

Typical causative bacteria of vaginitis reported so far is *Gardnerella vaginalis* and typical causative yeast of vaginitis reported is *Candida albicans*, but recently, it has been reported that *Sneathia* spp. strains are closely associated with the infection of human papillomavirus and preterm birth, that they may also act as vaginitis pathogens in the disturbed vaginal microflora. Accordingly, there is a need to find *Lactobacillus* lactic acid bacteria having an inhibitory effect on the growth of *Sneathia* spp. pathogens, in addition to previously known pathogens for vaginitis.

DISCLOSURE

Technical Problem

In the present invention, 190 strains of *Lactobacillus* spp. isolated from healthy women were screened for the inhibitory activity of pathogenic vaginal microorganisms. Probiotic *Lactobacillus* strains having novel activity have been found through the detection of *Lactobacillus* strains having an inhibitory effect against *Sneathia* spp. strains, which have been reported as microbiological markers associated with human papillomavirus infection and vaginitis-inducing causative bacteria, and a comprehensive inhibitory effect on the occurrence of vaginitis has been confirmed.

Accordingly, it is one object of the present invention to provide a *Lactobacillus* sp. strain having an activity to inhibit the growth of pathogenic vaginal microorganisms.

It is another object of the present invention to provide a pharmaceutical composition for treating and/or preventing diseases associated with the growth of pathogenic vaginal microorganisms, for example, vaginitis, containing the *Lactobacillus* sp. strain as an active ingredient.

It is still another object of the present invention to provide a method for preventing and/or treating diseases associated with the growth of pathogenic vaginal microorganisms which comprises administering the *Lactobacillus* sp. strain to a patient having diseases associated with the growth of pathogenic vaginal microorganisms.

It is further another object of the present invention to provide a health functional food or a cleansing product, etc., for improving, treating and/or preventing diseases associated with the growth of pathogenic vaginal microorganisms, for example, vaginitis, comprising the *Lactobacillus* sp. strain as an active ingredient.

Technical Solution

In order to achieve the objects above, the present invention provides a novel *Lactobacillus* sp. strain having an inhibitory effect on the growth of pathogenic vaginal microorganisms, and a pharmaceutical composition, a health functional food or a cleansing product comprising the same as an active ingredient.

One embodiment of the present invention relates to a *Lactobacillus* sp. strain which is characterized by having an inhibitory activity on the growth of pathogenic vaginal microorganisms.

The *Lactobacillus* sp. strain is isolated from the vaginal microflora of healthy women, and for example, it may be at least one *Lactobacillus* sp. strain selected from the group consisting of *Lactobacillus crispatus* SNUV 220, *Lactoba-*

*cillus fermentum* SNUV 175, *Lactobacillus jensenii* SNUV 360, and *Lactobacillus gasseri* SNUV 281.

The pathogenic vaginal microorganism may be at least one selected from the group consisting of fungi, bacteria and viruses. For example, it may be at least one selected from the group consisting of a *Candida* sp. strain being a causative yeast of Candidal vaginitis, *Sneathia* spp. strains associated with the occurrence of bacterial vaginitis, a *Gardnerella* sp. strain, a vaginitis pathogen, and human papillomavirus associated with human papillomavirus-infection. The *Lactobacillus* spp. strains may exhibit growth inhibitory effects against each of these strains or simultaneously and thus can be used for the prevention and/or treatment of female vaginitis.

Moreover, the *Candida* sp. strain may be *Candida albicans*, but is not limited thereto. The *Gardnerella* sp. strain may be *Gardnerella vaginalis*, but is not limited thereto. The *Sneathia* spp. strain may be *Sneathia amnii* and *Sneathia sanguinegens*, but is not limited thereto.

Further, the *Lactobacillus* sp. strain may function to actively produce hydrogen peroxide, and may also have acid resistance and bile resistance, but is not limited thereto.

The hydrogen peroxide activity of the *Lactobacillus* sp. strain can be qualitatively discriminated for the strains that induces dark green color change, when cultured in TMB medium in which 3,3',5,5'-tetramethylbenzidine (250 mg/L), hemin (5 mg/L) and vitamin K (0.5 ug/L) are added to MRS agar medium for *Lactobacillus* culture.

The acid resistance of the strains is determined based on the change in the growth rate when cultured in an acidic broth having a pH 2 and a pH 3 for 24 hours, and the bile resistance is determined based on the change in the growth rate when cultured for 24 hours in a broth supplemented with bile salt with a concentration ranging from 0.1% to 4% (w/v).

The *Lactobacillus* sp. strain may exhibit a survival rate of 50% or higher at a concentration of 0.1% (w/v) bile salt, but is not limited thereto.

Another embodiment of the present invention relates to a growth inhibitor of pathogenic vaginal microorganisms containing *Lactobacillus* sp. strain as an active ingredient, and a pharmaceutical composition for treating and/or preventing vaginitis, a food composition or cleansing product for improving, preventing or treating vaginitis including the inhibitor.

The *Lactobacillus* sp. strain may be *Lactobacillus crispatus, Lactobacillus fermentum, Lactobacillus jensenii*, and *Lactobacillus gasseri*.

Specifically, the strain may be at least one *Lactobacillus* sp. strain selected from the group consisting of *Lactobacillus crispatus* SNUV 220 deposited under accession No. KCTC18374P, *Lactobacillus fermentum* SNUV 175 deposited under accession No. KCTC18371P, *Lactobacillus jensenii* SNUV 360 deposited under accession No. KCTC18372P, *Lactobacillus gasseri* SNUV 281 deposited under accession No. KCTC18375P These strains were deposited with the Korean Collection for Type Cultures located in Yuseong-gu, Daejeon, South Korea on Apr. 7 and 9, 2015 and the accession numbers thereof were assigned.

The growth inhibitor of vaginitis pathogens containing the *Lactobacillus* sp. strain according to the present invention as an active ingredient exhibits antiviral activity, antifungal activity against fungal pathogens, and antimicrobial activity against bacteria, and the vaginitis pathogens may be caused by at least one strain selected from the group consisting of a *Candida* sp. strain, a *Gardnerella* sp. strain, and a *Sneathia* spp. strain.

For example, the *Candida* sp. strain may be *Candida albicans*, but is not limited thereto. Further, the *Gardnerella* sp. strain may be *Gardnerella vaginalis*, but is not limited sp. strain may be *Gardnerella vaginalis*, but is not limited thereto. Furthermore, the *Sneathia* spp. strain may be *Sneathia amnii* and *Sneathia sanguinegens*, but is not limited thereto The pharmaceutical composition according to the present invention can be administered to mammals including human via various routes. The mode of administration may be any mode commonly used in the art. For example, it may be administered by oral, transdermal, intravenous, intramuscular, subcutaneous routes or the like, and preferably, it may be orally administered.

The pharmaceutical composition of the present invention may be used after being formulated into an oral preparation, such as powders, granules, tablets, capsules, suspensions, emulsions, syrups, and aerosols, etc., and a parental preparation, such as epidermal formulations, suppositories, or sterile injection solutions, in accordance with a conventional method The pharmaceutical composition of the present invention may further contain pharmaceutically suitable and physiologically acceptable adjuvants such as carriers, excipients and diluents, etc.

Examples of carriers, excipients and diluents that can be included in the pharmaceutical composition of the present invention, may include lactose, dextrose, sucrose, sorbitol, mannitol, xylitol, erythritol, maltitol, starch, acacia gum, alginate, gelatin, calcium phosphate, calcium silicate, cellulose, methylcellulose, microcrystalline cellulose, polyvinyl pyrrolidone, water, methyl hydroxybenzoate, propyl hydroxybenzoate, talc, magnesium stearate, and mineral oil. When formulated into a preparation, a diluting agent or an excipient, such as commonly-used fillers, weighting agents, binding agents, wetting agents, disintegrating agents, and surfactants can be used.

When the pharmaceutical composition for preventing and/or treating vaginitis according to the present invention is provided for parenteral administration, for example, topical preparations such as liquid preparation, gel preparation, cleansing composition, tablet for vagal insertion, suppository, cream, ointment, dressing solution, spray, other coating agents, etc., liquid preparations such as solution-type, suspension-type, emulsion-type preparation, etc., and external skin formulations such as sterile aqueous solution, non-aqueous solvent, suspension, emulsion, freeze-drying preparation, suppository, cream, ointment, jelly, foam, cleansing agent or vaginal insert, preferably, liquid preparation, gel preparation, cleansing composition, tablet for vagal insertion, etc., may be included. The formulation can be prepared, for example, by adding a dissolution adjuvant, an emulsifying agent, a buffering agent for pH control, etc., to sterilized water.

The non-aqueous solvents and suspending agents may include vegetable oils such as propylene glycol, polyethylene glycol and olive oil, and an injectable ester such as ethyl oleate and the like.

In an embodiment where the pharmaceutical composition of the present invention is applied to humans, the pharmaceutical composition of the present invention may be administered alone, but considering the mode of administration and the standard pharmaceutical practice, it can be generally administered by mixing with the selected pharmaceutical carrier.

For example, the composition containing the *Lactobacillus* sp. strain of the present invention may be orally, intrabuccally, or sublingually administered in a tablet form containing starch or lactose, in a capsule form containing only the active ingredient according to the present invention or containing an excipient in addition to the active ingredient, or in an elixir or suspension form containing a chemical agent for flavor or color.

The dose of the pharmaceutical composition containing the *Lactobacillus* sp. strain of the present invention may vary depending on the patient's age, weight, sex, dosage form, health condition and severity of disease. In addition, it can be administered in divided doses once to several times a day at fixed time intervals according to the decision of a doctor or pharmacist. For example, the daily dose may be 0.1 to 500 mg/kg, preferably 0.5 to 300 mg/kg, based on the content of the active ingredient. The above doses are exemplified as an average case, and its dose may increase or decrease depending on individual differences. If the daily dose of the composition containing the mixture extract of the present invention is less than the above-mentioned dose, a significant effect cannot be obtained. If the daily dose exceeds the above-mentioned range, not only it is non-economical, but also it may cause undesirable side effects as the dose deviates from the above range.

Still another embodiment of the present invention provides a health functional food for improving, treating and/or preventing vaginitis containing the *Lactobacillus* sp. strain as an active ingredient. The health functional food may be various beverages, fermented milk, food additives, and the like. The *Lactobacillus* sp. strain is as described above.

The content of the *Lactobacillus* sp. strain as an effective ingredient contained in the health functional food is not particularly limited, but may appropriately vary depending on the form of food, desired use or the like. For example, it may be added in an amount of 0.01 to 15% by weight based on the total weight of the food, and the health beverage composition may be added at a ratio of 0.02 to 10 g, preferably 0.3 to 1 g, based on 100 ml.

In the beverage among the health functional food of the present invention, there is no particular limitation on the liquid ingredient, except that the *Lactobacillus* strain is contained as an essential ingredient at the indicated ratio, and various flavoring agents or natural carbohydrates may be contained as additional ingredients as in common beverages.

Examples of the above-mentioned natural carbohydrates include common sugars including monosaccharides, such as glucose, fructose, etc., disaccharides, such as maltose, sucrose, etc., and polysaccharides, such as dextrin, cyclodextrin, etc., as well as sugar alcohols, such as xylitol, sorbitol, erythritol, etc. As flavoring agents other than those mentioned above, natural flavoring agents (thaumatin, *stevia* extract (for example, rebaudioside A, glycyrrhizin, etc.) and synthetic flavoring agents (saccharin, aspartame, etc.) may be favorably used. The ratio of the natural carbohydrate is generally about 1 to 20 g, preferably about 5 to 12 g, per 100 ml of the composition of the present invention.

In addition to the above, the health functional food of the present invention may contain various nutrients, vitamins, minerals (electrolyte), flavoring agents such as synthetic flavoring agents and natural flavoring agents, coloring agents and flavor enhancers (cheese, chocolate, etc.), pectic acid and salts thereof, alginic acid and salts thereof, organic acids, protective colloidal thickening agents, pH controlling agents, stabilizing agents, preservatives, glycerin, alcohol, carbonizing agents as used in carbonated beverages and the like.

Moreover, the health functional food of the present invention may contain fruits, as used in preparing natural fruit juices and fruit juice beverages and vegetable beverages. These components can be used independently or in combination. Although the proportion of these additives is not of great importance, it is generally selected from a range of 0 to about 20 parts by weight per 100 parts by weight of the health functional food of the present invention.

Still another embodiment of the present invention provides a cleansing product for improving, treating and/or preventing vaginitis containing the *Lactobacillus* sp. strain as an active ingredient. The cleansing product may be a solid cosmetic soap, a hand cleaner, a liquid shampoo, a liquid soap, a liquid conditioner, a body cleaner, a creamy soap, or the like. The *Lactobacillus* sp. strain is as described above.

The cleansing product may further include a carrier for formulating a preparation. Examples of the carrier include a binding agent, a lubricant, an agent for suspension, a solubilizing agent, a buffer, a preservative, a lubricant, an isotonic agent, an excipient, a stabilizer, a dispersant, a suspending agent, a coloring agent, a flavoring agent, etc.

Advantageous Effects

The present invention relates to a novel *Lactobacillus* sp. strain having an ability to inhibit the growth of pathogenic vaginal microorganisms, and a pharmaceutical composition, a health functional food, and a cleansing product containing the same as an active ingredient. Therefore, the present invention exhibits an activity to inhibit the growth of *Sneathia* spp. pathogens associated with the human papillomavirus (HPV) infection and the occurrence of bacterial vaginitis, and an inhibitory effect on the growth of *Gardnerella vaginalis* which is a vaginitis pathogen, and *Candida albicans* which is a causative yeast of Candidal vaginitis, and thus can be used for the improvement, prevention and/or treatment of female vaginitis.

BRIEF DESCRIPTION OF DRAWINGS

FIG. 5 is a graph showing the results of univariate analysis of microorganism groups with a significant change for each group, which are the results of microbiome analysis after vaginal administration of four types of *Lactobacillus* strains according to one embodiment of the present invention into a mouse animal model infected with *Gardnerella vaginalis*.

DETAILED DESCRIPTION OF THE EMBODIMENTS

Figure 1:
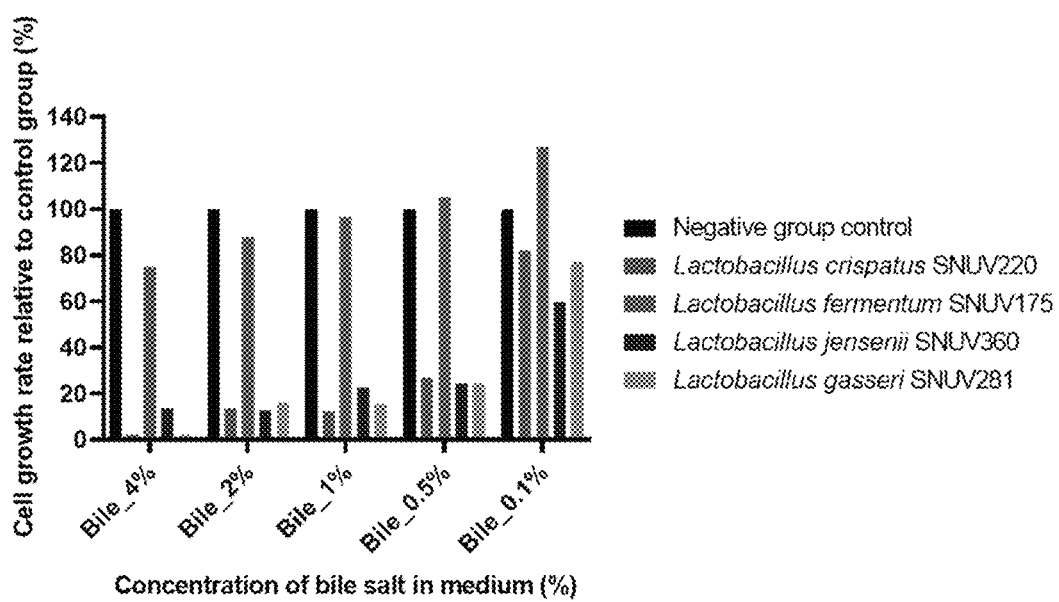
FIG. 1 is a graph showing the measurement results of bile resistance by confirming the growth rate after culturing for 24 hours in a medium containing 0.1% to 4% (w/v) of bile salt according to one embodiment of the present invention.

Hereinafter, the present invention will be described in more detail by way of Examples. However, these Examples are given for illustrative purposes only, and the scope of the invention is not intended to be limited by these Examples.

Example 1. Isolation and Identification of Strains

About 190 different *Lactobacillus* strains were isolated from the vaginal microflora of healthy women. Specifically, the samples for the isolation of vaginal microflora were obtained from nine subjects, including three pairs of identical twins and their mothers who participated in the Korean Twin-Family Cohort Study, and were supplied from Samsung Hospital in the form of mid-vaginal swab samples (IRB No. 144-2011-07-11).

The swab samples were transferred to the present laboratory in the form of being stored in a refrigerator within 4 hours after collection in a modified Liquid Amies solution and immediately used for the isolation of strains. The samples were sequentially diluted from 10-1 times to 10-8 times and spread on three different media of Chocolate agar, Rogosa agar, and Columbia agar, and cultured for 48 hours under anaerobic conditions.

After the culture, purely isolated colonies were randomly selected and subjected to shake culture in brain heart infusion (BHI) broth containing 5% human serum. Genomic DNA was extracted from the cells, and PCR reaction was carried out using UnivFwd (5'-AGA GTT TGA TCM TGG CTC AG-3'; SEQ ID NO: 5) primer and UnivRev (5'-GGY TAC CTT GTT ACG ACT T-3'; SEQ ID NO: 6) primer for 16S ribosomal RNA typing. The PCR products were purified using QIAquick PCR purification kit and subjected to sequence analysis using ABI3711 automatic sequencer.

The results are the same as those shown in Tables 1 and 2 below. Using such sequence information, the identification of the strains was finally completed by comparing with BLAST program of Genbank (www.ncbi.nlm.nhi.gov) and ExTaxon database program (www.ezbiocloud.net/eztaxon), together with the identification data of the previous result report.

TABLE 1

| Species | Name | Nucleotide sequence (5'→3') | SEQ ID NO |
|---|---|---|---|
| Lacto-bacillus crispatus | SNUV 220 | TTACTTCGGCAATGACGTTAGGAAAGCGAGCGG CGGATGGGTGAGTAACACGTGGGGAACCTGCCC CATAGTCTGGGATACCACTTGGAAACAGGTGCT AATACCGGATAAGAAAGCAGATCGCATGATCAG CTTTTAAAAGGCGGCGTAAGCTGTCGCTATGGG ATGGCCCCGCGGTGCATTAGCTAGTTGGTAAGG TAAAGGCTTACCAAGGCGATGATGCATAGCCGA GTTGAGAGACTGATCGGCCACATTGGGACTGAG ACACGGCCCAAACTCCTACGGGAGGCAGCAGTA GGGAATCTTCCACAATGGACGCAAGTCTGATGG AGCAACGCCGCGTGAGTGAAGAAGGTTTTCGGA TCGTAAAGCTCTGTTGTTGGTGAAGAAGGATAG AGGTAGTAACTGGCCTTTATTTGACGGTAATCA ACCAGAAAGTCACGGCTAACTACGTGCCAGCA | 1 |

TABLE 1-continued

| Species | Name | Nucleotide sequence (5'→3') | SEQ ID NO |
|---|---|---|---|
| | | CCGCGGTAATACGTAGGTGGCAAGCGTTGTCCG GATTTATTGGGCGTAAAGCGAGCGCAGGCGGAA GAATAAGTCTGATGTGAAAGCCCTCGGCTTAAC CGAGGAACTGCATCGGAAACTGTTTTTCTTGAG TGCAGAAGAGGAGAGTGGAACTCCATGTGTAGC GGTGGAATGCGTAGATATATGGAAGAACACCAG TGGCGAAGGCGGCTCTCTGGTCTGCAACTGACG CTGAGGCTCGAAAGCATGGGTAGCGAACAGGAT TAGATACCCTGGTAGTCCATGCCGTAAACGATG AGTGCTAAGTGTTGGGAGGTTTCCGCCTCTCAG TGCTGCAGCTAACGCATTAAGCACTCCGCCTGG GGAGTACGACCGCAAGGTTGAAACTCAAAGGAA TTGACGGGGGCCCGCACAAGCGGTGGAGCATGT GGTTTAATTCGAAGCAACGCGAAGAACCTTACC AGGTCTTGACATCTAGTGCC | |
| Lacto-bacillus fermentum | SNUV 175 | CTGCCCAGAAGCGGGGACAACATTTGGAAACA GATGCTAATACCGCATAACAACGTTGTTCGCAT GAACAACGCTTAAAAGATGGCTTCTCGCTATCA CTTCTGGATGGACCTGCGGTGCATTAGCTTGTT GGTGGGGTAACGGCCTACCAAGGCGATGATGCA TAGCCGAGTTGAGAGACTGATCGGCCACAATGG GACTGAGACACGGCCCATACTCCTACGGGAGGC AGCAGTAGGGAATCTTCCACAATGGGCGCAAGC CTGATGGAGCAACACCGCGTGAGTGAAGAAGGG TTTCGGCTCGTAAAGCTCTGTTGTTAAAGAAGA ACACGTATGAGAGTAACTGTTCATACGTTGACG GTATTTAACCAGAAAGTCACGGCTAACTACGTG CCAGCAGCCGCGGTAATACGTAGGTGGCAAGCG TTATCCGGATTTATTGGGCGTAAAGAGAGTGCA GGCGGTTTTCTAAGTCTGATGTGAAAGCCTTCG GCTTAACCGGAGAAGTGCATCGGAAACTGGATA ACTTGAGTGCAGAAGAGGGTAGTGGAACTCCAT GTGTAGCGGTGGAATGCGTAGATATATGGAAGA ACACCAGTGGCGAAGGCGGCTACCTGGTCTGCA ACTGACGCTGAGACTCGAAAGCATGGGTAGCGA ACAGGATTAGATACCCTGGTAGTCCATGCCGTA AACGATGAGTGCTAGGTGTTGGG | 2 |

TABLE 2

| Species | Name | Nucleotide sequence (5'→3') | SEQ ID NO |
|---|---|---|---|
| Lacto-bacillus jensenii | SNUV 360 | AAAAGCTACTTTCGCATGAAAGAAGTTTAAAAG GCGGCGTAAGCTGTCGCTAAAGGATGGACCTGC GATGCATTAGCTAGTTGGTAAGGTAACGGCTTA CCAAGGCGATGATGCATAGCCGAGTTGAGAGAC TGATCGGCCACATTGGGACTGAGACACGGCCCA AACTCCTACGGGAGGCAGCAGTAGGGAATCTTC CACAATGGACGAAAGTCTGATGGAGCAACGCCG CGTGAGTGAAGAAGGTTTTCGGATCGTAAAGCT CTGTTGTTGGTGAAGAAGGATAGAGGTAGTAAC TGGCCTTTATTTGACGGTAATCAACCAGAAAGT CACGGCTAACTACGTGCCAGCAGCCGCGGTAAT ACGTAGGTGGCAAGCGTTGTCCGGATTTATTGG GCGTAAAGCGAGCGCAGGCGGATTGATAAGTCT GATGTGAAAGCCTTCGGCTCAACCGAAGAACTG CATCAGAAACTGTCAATCTTGAGTGCAGAAGAG GAGAGTGGAACTCCATGTGTAGCGGTGGAATGC GTAGATATATGGAAGAACACCAGTGGCGAAGGC GGCTCTCTGGTCTGTAACTGACGCTGAGGCTCG AAAGCATGGGTAGCGAACAGGATTAGATACCCT GGTAGTCCATGCCGTAAACGATGAGTGCTAAGT GTTGGGAGGTTTCCGCCTCTCAGTGCTGCAGCT AACGCATTAAGCACTCCGCCTGGGG | 3 |
| Lacto-bacillus gasseri | SNUV 281 | CGGATAACAACACTAGACGCATGTCTAGAGTTT AAAAGATGGTTCTGCTATCACTCTTGGATGGAC CTGCGGTGCATTAGCTAGTTGGTAAGGCAACGG CTTACCAAGGCAATGATGCATAGCCGAGTTGAG AGACTGATCGGCCACATTGGGACTGAGACACGG CCCAAACTCCTACGGGAGGCAGCAGTAGGGAAT | 4 |

TABLE 2-continued

| Species | Name | Nucleotide sequence (5'→3') | SEQ ID NO |
|---|---|---|---|
| | | CTTCCACAATGGACGCAAGTCTGATGGAGCAAC<br>GCCGCGTGAGTGAAGAAGGGTTTCGGCTCGTAA<br>AGCTCTGTTGGTAGTGAAGAAAGATAGAGGTAG<br>TAACTGGCCTTTATTTGACGGTAATTACTTAGA<br>AAGTCACGGCTAACTACGTGCCAGCAGCCGCGG<br>TAATACGTAGGTGGCAAGCGTTGTCCGGATTTA<br>TTGGGCGTAAAGCGAGTGCAGGCGGTTCAATAA<br>GTCTGATGTGAAAGCCTTCGGCTCAACCGGAGA<br>ATTGCATCAGAAACTGTTGAACTTGAGTGCAGA<br>AGAGGAGAGTGGAACTCCATGTGTAGCGGTGGA<br>ATGCGTAGATATATGGAAGAACACCAGTGGCGA<br>AGGCGGCTCTCTGGTCTGCAACTGACGCTGAGG<br>CTCGAAAGCATGGGTAGCGAACAGGATTAGATA<br>CCCTGGTAGTCCATGCCGTAAACGATGAGTGCT<br>AAGTGTTGGGAGGTTTCCGCCTCTCAGTGCTGC<br>AGCTAACGCATTAAGCACTCCGCCTGGGG | 5 |

TABLE 3

| Name | Taxonomy | Accession | Pairwise Similarity (%) | Diff/Total nt | Completeness (%) |
|---|---|---|---|---|---|
| SNUV 220 | Bacteria; Firmicutes; Bacilli; Lactobacillales; Lactobacillaceae; Lactobacillus; Lactobacillus crispatus; | Y17362 | 100 | 0/650 | 100 |
| SNUV 175 | Bacteria; Firmicutes; Bacilli; Lactobacillales; Lactobacillaceae; Lactobacillus; Lactobacillus fermentum; | AP008937 | 99.86 | 1/715 | 100 |
| | Bacteria; Firmicutes; Bacilli; Lactobacillales; Lactobacillaceae; Lactobacillus; Lactobacillus fermentum; | AJ575812 | 99.86 | 1/715 | 100 |
| SNUV 360 | Bacteria; Firmicutes; Bacilli; Lactobacillales; Lactobacillaceae; Lactobacillus; Lactobacillus jensenii; | AF243176 | 99.86 | 1/718 | 98.9 |
| | Bacteria; Firmicutes; Bacilli; Lactobacillales; Lactobacillaceae; Lactobacillus; Lactobacillus fornicalis; | Y18654 | 99.86 | 1/717 | 95.5 |
| SNUV 281 | Bacteria; Firmicutes; Bacilli; Lactobacillales; Lactobacillaceae; Lactobacillus; Lactobacillus gasseri; | CP000413 | 99.86 | 1/722 | 100 |

As shown in Tables 1 to 3, the results were found to be *Lactobacillus crispatus, Lactobacillus fermentum, Lactobacillus jensenii,* and *Lactobacillus gasseri*, respectively. Accordingly, they were assigned SNUV 220, SNUV 175, SNUV 360, and SNUV 281, respectively, and deposited with the Korean Collection for Type Cultures (KCTC) located in Yuseong-gu, Daejeon, South Korea and were assigned accession numbers KCTC18374P (SNUV 220, deposited on April 9), KCTC18371P (SNUV 175, deposited on April 7), KCTC18372P (SNUV 360, deposited on April 7) and KCTC18375P (SNUV 281, deposited on April 9).

For pure isolation and long-term storage of the identified strains, glycerol (16% v/v) was added to the culture medium that reached the exponential phase, and stored at −80° C. as a stock. In order to prepare cell culture medium for the evaluation of inhibitory activity of vaginitis pathogens for each strain, 1% of each strain was inoculated in an anaerobic MRS medium and cultured at 37° C. for 24 hours. Then, the microbial cells were removed by centrifugation at 13000×g for 10 minutes, and the supernatant was passed through a membrane filter with a pore size of 0.22 um and then stored at −80° C. until they were used in the experiment.

Example 2. Disk Inhibition Assay

Each of *Lactobacillus* strains isolated in Example 1 was used for the assay by culturing at 37° C. for 20 hours using MRS broth (Difco, USA). The strains of *Sneathia* spp. and *Gardnerella vaginalis* were inoculated into New York City III (NYCIII) broth and then anaerobically cultured at 37° C. for 48 hours or 24 hours, respectively, and used in the experiment.

As for the *Sneathia* spp. strains used in the experiment, two kinds of strains of *Sneathia* spp., which was isolated in Virginia Commonwealth University School of Medicine and has been reported in the paper, and *Sneathia sanguinegens* that the present inventors isolated from Korean women were used. As the *Gardnerella vaginalis* strain used in the experiment, KCTC 5096 strain furnished from the Korean Collection for Type Cultures (KCTC) was used.

After dispensing and solidifying 15 ml of MRS agar medium on a plate, 7 ml of New York City III (NYCIII) soft agar medium (0.75% agar) inoculated with the strains of *Sneathia* spp. and *Gardnerella vaginalis* at a density of 5×10$^6$ CFU/mL was formed as multilayer medium. Once the upper soft agar medium had been solidified, a diffusion paper disc (8 mm in diameter) was placed on the medium, and about 20 ul of culture product of each *Lactobacillus* strain was absorbed thereto. Then, the plate was added to an anaerobic jar and anaerobically incubated at 37° C. for 48 hours. After the incubation, the growth inhibitory zone of the strains of *Sneathia* spp. and *Gardnerella vaginalis* appearing around the disk was measured. The inhibitory activity was expressed as the diameter (mm) of the transparent disk in which the growth of the strains was inhibited from the center of the disk.

The disk inhibition assay was performed against the strains of *Sneathia* spp. and *Gardnerella vaginalis* with culture supernatant of isolated *Lactobacillus* strains, and the representative result are shown in Table 4 below.

TABLE 4

| | | disk inhibition (diameter, mm) | | |
|---|---|---|---|---|
| Species | Isolates_No | Sn. Amnii | Sn. Sanguinegens | G. vaginalis |
| Lactobacillus crispatus | SNUV 220 | 23 | 46 | 19 |
| Lactobacillus fermentum | SNUV 175 | — | 19 | — |
| Lactobacillus jensenii | SNUV 360 | 60 | 60 | 25 |
| Lactobacillus gasseri | SNUV 281 | — | 23 | 19 |
| Lactobacillus crispatus | SNUV 215 | — | — | — |
| Lactobacillus fermentum | SNUV 110 | — | — | — |
| Lactobacillus jensenii | SNUV 212 | — | — | — |
| Lactobacillus gasseri | SNUV 445 | — | — | — |

As can be confirmed in Table 4, although the size of disk inhibition of the *Lactobacillus* culture supernatant was slightly different depending on the type of the inhibitory strains, four types of *Lactobacillus* isolated strains which simultaneously inhibited the growth of *Sneathia* spp. and *Gardnerella vaginalis* strains, that is, *Lactobacillus crispatus* SNUV 220, *Lactobacillus fermentum* SNUV 175, *Lactobacillus jensenii* SNUV 360, and *Lactobacillus gasseri* SNUV 281 were selected. In particular, the *Lactobacillus jensenii* SNUV 360 strain exhibited a most potent inhibitory activity against both strains of *Sneathia* spp. and *Gardnerella* sp.

Example 3. Inhibitory Activity of *Lactobacillus* Isolates Against *Candida albicans*

In order to confirm the inhibitory activity against *Candida albicans* strain, which is a causative yeast of Candidal vaginitis of the four kinds of *Lactobacillus* strains screened in Example 2 above, *Candida albicans* ATCC44858 strain (American Type Culture Collection), and MYA4788 strain (American Type Culture Collection), which has been proven to cause vaginitis in animal experiments, were selected as target strains for selection of *Lactobacillus* isolates having an inhibitory function, and the experiments was conducted accordingly.

Specifically, the *Candida albicans* strains were evaluated using a 96-well diffusion test. For the experiment, 50 ul of *Candida albicans* ATCC44858 (or *Candida albicans* M4788) culture media diluted by adding 100 ul of Yeast Malt (YM) medium and 100 ul of *Lactobacillus* culture supernatant was added to a well of 96-well plate, and then cultured at 37° C. for 24 hours. Thereafter, the growth of inhibited *Candida* strains was estimated by measurement of absorbance at 600 nm, and the results are shown in Table 5.

TABLE 5

| Species | Isolates_No | Candida 44858 (co-culture) | Candida MYA4788 (co-culture) |
|---|---|---|---|
| Negative control group | | 1 | 1 |
| Lactobacillus crispatus | SNUV 220 | 0.028 | 0.007 |
| Lactobacillus fermentum | SNUV 175 | — | 0.003 |
| Lactobacillus jensenii | SNUV 360 | — | 0.007 |
| Lactobacillus gasseri | SNUV 281 | 0.012 | 0.010 | optical density after 24 h (O.D. at 600 nm)

As can be confirmed in Table 5, all the selected *Lactobacillus crispatus* SNUV 220, *Lactobacillus fermentum* SNUV 175, *Lactobacillus jensenii* SNUV 360, and *Lactobacillus gasseri* SNUV 281 had a killing activity against *Candida* strains close to 100%. Accordingly, all four isolated strains have been shown to have a significant effect on the prevention of vaginitis.

Example 4. Hydrogen Peroxide-Producing Activity of *Lactobacillus* Isolates

In order to investigate the degree of hydrogen peroxide production, a Tetramethylbenzidine (TMB) agar medium was prepared as shown in Table 6 below (medium composition per 1 L).

TABLE 6

| Difco *Lactobacilli* MRS medium | 55 g |
|---|---|
| TMB | 250 mg |
| Starch, soluble | 100 g |
| Hemnin solution | 10 mL |
| Vitamin K solution | 0.2 mL |
| Peroxidase solution (1 mg/mL) | 10 mL |

Subsequently, each of *Lactobacillus crispatus* SNUV 220, *Lactobacillus fermentum* SNUV 175, *Lactobacillus jensenii* SNUV 360, and *Lactobacillus gasseri* SNUV 281, which are the four types of *Lactobacillus* strains screened in Example 2, was cultured in MRS broth at 37° C. for 20 hours, inoculated onto the TMB agar plate, and then anaerobically cultured at 37° C. for 2 days. After the culture, the plate was exposed to the air for 30 minutes and evaluated via a qualitative experiment in which the color of the colonies turns to blue. The extent to which the color of colonies turned to blue was observed with the naked eye, and the results are shown in Table 7 below.

TABLE 7

| Species | Isolates_No | $H_2O_2$ production |
|---|---|---|
| Lactobacillus crispatus | SNUV 220 | − |
| Lactobacillus fermentum | SNUV 175 | +++ |
| Lactobacillus jensenii | SNUV 360 | +++ |
| Lactobacillus gasseri | SNUV 281 | ++ |

As can be confirmed in Table 7, the hydrogen peroxide-producing activity of each strain showed a different pattern, and it was confirmed that the production of hydrogen peroxide actively occurred in *Lactobacillus fermentum* SNUV 175, *Lactobacillus jensenii* SNUV 360, and *Lactobacillus gasseri* SNUV 281. Accordingly, the inhibitory activity of the selected strains is expected to show a difference in the mechanism of action.

Example 5. Evaluation of Acid Resistance of *Lactobacillus* Isolates

The acid resistance of the strains was determined by comparing the growth rate when cultured at 37° C. for 24 hours in acidic broth prepared by titrating MRS broth (pH 6.7) to pH 2 and pH 3, and the growth rate under basic broth conditions of pH 6.7, and the results are shown in Table 8 below.

TABLE 8

| Species | Isolates_No | pH 6.7 | pH 3 | pH 2 |
|---|---|---|---|---|
| Lactobacillus crispatus | SNUV 220 | +++ | + | − |
| Lactobacillus fermentum | SNUV 175 | +++ | +++ | + |
| Lactobacillus jensenii | SNUV 360 | +++ | + | − |
| Lactobacillus gasseri | SNUV 281 | ++ | + | + |

As can be confirmed in Table 8, all four strains showed the growth under the culture conditions of pH 3, and in particular, SNUV 175 strain and SNUV 281 strain showed the growth even under the condition of pH 2, indicating that they have a strong acid resistance.

Example 6. Evaluation of Bile Resistance in *Lactobacillus* Isolates

For the evaluation of bile resistance, the growth rate of *Lactobacillus* isolates was measured after culturing in the media containing 0.1% to 4% of bile salt for 24 hours or more, and the results are shown in Table 9 and FIG. 1.

TABLE 9

| Species | bile salts 4% | bile salts 2% | bile salts 1% | bile salts 0.5% | bile salts 0.1% |
|---|---|---|---|---|---|
| Negative control group | 100 | 100 | 100 | 100 | 100 |
| *Lactobacillus crispatus* SNUV 220 | 2.1 | 13.7 | 12.1 | 27.0 | 81.8 |
| *Lactobacillus fermentum* SNUV 175 | 75.1 | 88.0 | 96.5 | 104.9 | 127.1 |
| *Lactobacillus jensenii* SNUV 360 | 13.5 | 12.6 | 22.8 | 24.1 | 59.3 |
| *Lactobacillus gasseri* SNUV 281 | 2.2 | 16.2 | 15.3 | 24.4 | 76.9 |

As can be confirmed in Table 9 and FIG. 1, all four strains generally showed a growth rate of 50% or higher at the concentration of 0.1% bile salt. In particular, *Lactobacillus fermentum* SNUV 175 strain maintained the growth rate of 104.9% to 75.1%, compared to the non-treatment group at the concentration ranging from 0.5% to 4% of bile salt, showing a very high resistance to bile acid. Accordingly, it is expected to maintain a high survival rate even when orally administered.

Example 7. Evaluation of Antibiotic Resistance in *Lactobacillus* Isolates

In order to confirm the safety when applied to functional food materials, etc., antibiotic resistance of the novel *Lactobacillus* sp. isolates having an activity to inhibit the growth of pathogenic vaginal microorganisms was evaluated. Currently, codes and standards concerning antibiotic resistance when utilizing *Lactobacillus*-based lactic acid bacteria in the food were not established, and thus it was evaluated based on the EFSA standard which is the international standard concerning antibiotic resistance of microorganisms added to animal feeds.

Specifically, the evaluation of the antibiotic resistance in *Lactobacillus* strains was performed according to the European Food Safety Authority (EFSA)'s guidelines for nine antibiotics including ampicillin (AMP), chloramphenicol (CHR), clindamycin (CLM), erythromycin (ERY), gentamycin (GEN), kanamycin (KAN), streptomycin (STR), tetracycline (TET), vancomycin (VAN) and the like. The test method used in the evaluation on the antibiotic resistance was performed according to ISO 10932:2010 (IDF 223: 2010), which is the SOP standard for antibiotic resistance test of lactic acid bacteria. Each *Lactobacillus* strain was inoculated at a density of ~6×10$^6$ CFU/mL in LAB susceptibility test medium (LSM)-broth (90% IsoSensitest- and 10% MRS-broth; Oxoid), and then MIC test strip (Liofilchem, Italy) for each antibiotic was placed thereon. The degree of inhibition and MIC were evaluated after anaerobic culture at 37° C. for 48 hours, and the results are shown in Table 10 and FIG. 2.

TABLE 10

| antibiotics | *L. jensenii* SNUV 360 | EFSA guideline | *L. fermentum* SNUV 175 | EFSA guideline |
|---|---|---|---|---|
| AMP | 0.094 | 1 | 0.125 | 2 |
| CHL | 3 | 4 | 2 | 4 |
| CLM | 0.38 | 1 | 0.064 | 1 |
| ERY | 0.19 | 1 | 0.38 | 1 |
| GEN | 2 | 16 | 1 | 16 |
| KAN | 4 | 16 | 24 | 32 |
| STR | 3 | 16 | 12 | 64 |
| TET | 0.75 | 4 | 2 | 8 |
| VAN | 0.5 | 2 | 64 | Not required |

Figure 2:
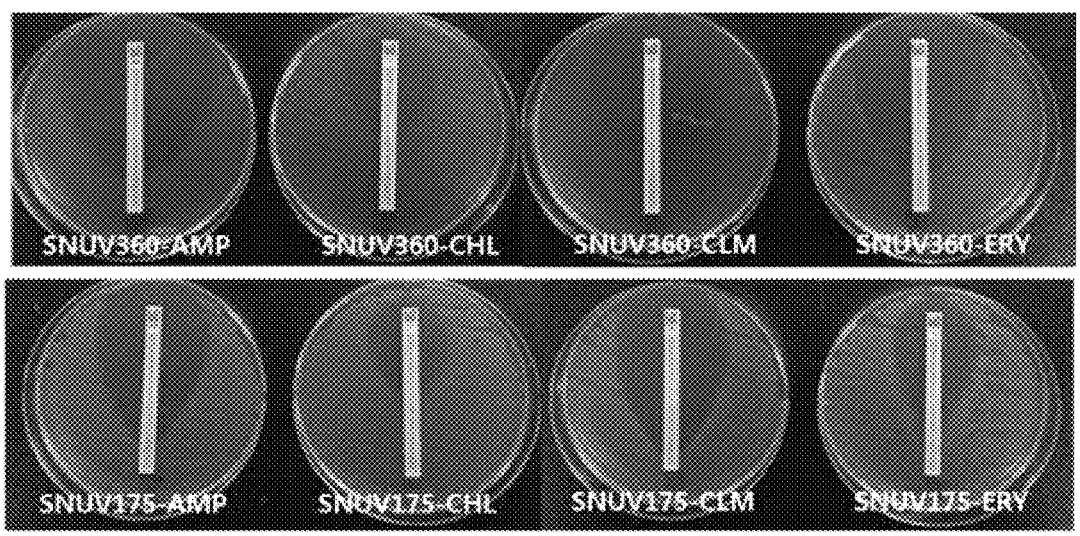
FIG. 2 is a representative graph showing the measurement results of antibiotic resistance of *Lactobacillus fermentum* SNUV 175 and *Lactobacillus jensenii* SNUV 360 according to one embodiment of the present invention against nine antibiotics.

As can be confirmed in Table 10 and FIG. 2, among the four isolation strains, *Lactobacillus jensenii* SNUV 360 and *Lactobacillus fermentum* SNUV 175 strains showed antibiotic susceptibility satisfying the EFSA criteria for all nine antibiotics used (EFSA guideline in Table 10), and thus it is expected to be used as a health functional food through oral administration Example 8. Evaluation of Inhibitory Activity of *Lactobacillus* Isolates on *Gardnerella vaginalis* Infection The hormone control and estrous cycle were induced by intraperitoneally injecting 0.5 mg of beta-esteradiol 3-benzonate to female mice (BALB/c mice). After three days, they were directly infected with *Gardnerella vaginalis* in the vagina at a concentration of 1×10$^7$ CFU per mouse to establish a vaginitis animal model.

Thereafter, four kinds of *Lactobacillus* isolates corresponding to 108 to 109 CFU per mouse were vaginally administered (7 mice per group). On day 2, the total bacterial DNA was extracted from the vaginal samples washed with 0.1 mL of PBS (Phosphate Buffered Saline) and microbiome community analysis was performed to measure the relative abundance of *Gardnerella vaginalis* and other vaginal microbiota. The DNA extraction from the vaginal fluid samples was performed using Mobio PowerSoil DNA extraction kit, and for the community analysis, the DNA was amplified via PCR using a primer corresponding to the V4 region of 16S rDNA, and next-generation sequencing analysis was carried out using Illumina Miseq equipment.

The analyzed sequences were subjected to microbiome analysis including taxon profile, α-diversity and β-diversity showing the difference in community structure between groups through Qiime pipeline, and the change in the amount of *Gardnerella vaginalis* pathogens upon the administration of *Lactobacillus* isolates was evaluated by calculating relative abundances (/% GV treatment group). The results are shown in Table 11 and FIGS. 3 to 5.

*Gardnerella vaginalis* treatment group, *Lactobacillus crispatus* SNUV 220 treatment group after infection with *Gardnerella vaginalis*, *Lactobacillus jensenii* SNUV 360 treatment group after infection with *Gardnerella vaginalis*, *Lactobacillus fermentum* SNUV 175 treatment group after infection with *Gardnerella vaginalis*, *Lactobacillus gasseri* SNUV 281 treatment group after infection with *Gardnerella vaginalis*, and metronidazole (0.75%) antibiotics treatment group as a positive control group after infection with *Gardnerella vaginalis* were designated as 'GV', 'SNUV 220', 'SNUV 360', 'SNUV 175', 'SNUV 281' and 'MTZ', respectively.

TABLE 11

| | Relative abundance (/% GV group) |
|---|---|
| GV | 100 |
| SNUV 220 | 18.0 |
| SNUV 360 | 5.3 |
| SNUV 175 | 2.6 |
| SNUV 281 | 6.9 |
| MTZ | 74.9 |

Figure 3:
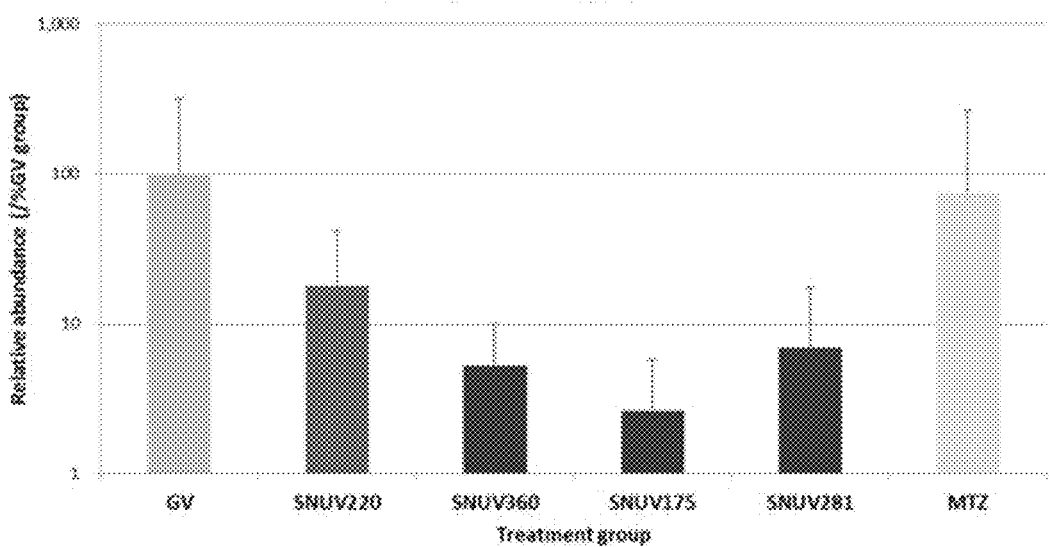
FIG. 3 is a graph showing the relative abundance of *Gardnerella vaginalis* for each treatment group, which is the result of microbiome analysis after vaginal administration of four types of *Lactobacillus* strains according to one embodiment of the present invention into a mouse animal model infected with *Gardnerella vaginalis*.

As can be confirmed in Table 11 and FIG. 3, the strains of *Lactobacillus crispatus* SNUV 220, *Lactobacillus jensenii* SNUV 360, *Lactobacillus fermentum* SNUV 175, *Lactobacillus gasseri* of the present invention have been found to reduce the amount of *Gardnerella vaginalis* pathogens in in vivo vaginitis model.

Figure 4:
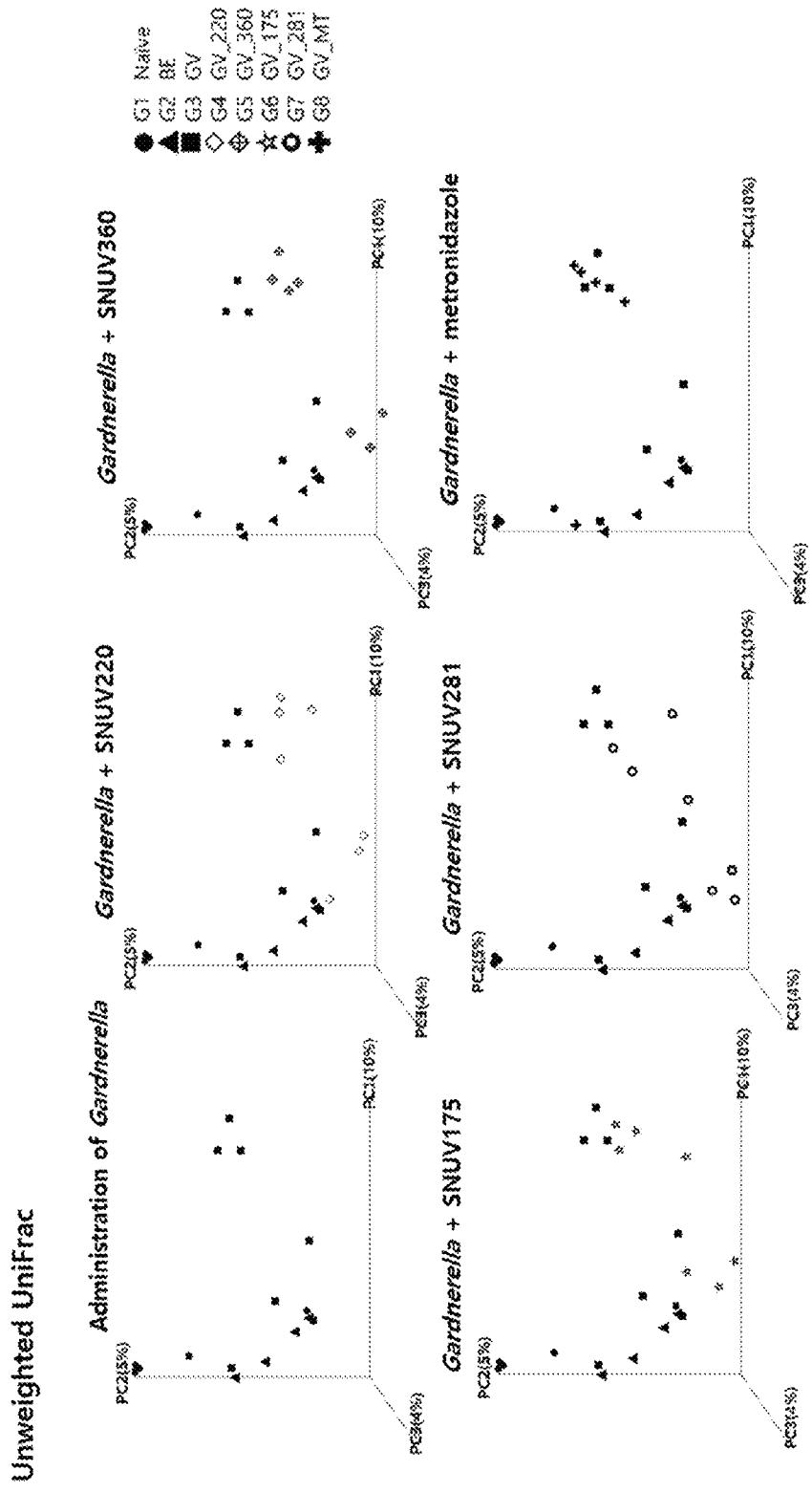
FIG. 4 is a principal component analysis (PCoA) graph showing the change in the community structure of vaginal microflora after 2 days of administration, which are the results of microbiome analysis after vaginal administration of four types of *Lactobacillus* strains according to one embodiment of the present invention into a mouse animal model infected with *Gardnerella vaginalis*.

As can be confirmed in FIG. 4, when the four *Lactobacillus* strains of the present invention were administered, it was found that the community structure of the vaginal microflora was all changed compared to *Gardnerella vaginalis*-infected control group. The changes in the community structure after administration of *Gardnerella* and *Lactobacillus* strains were measured using Unweighted UniFrac distance and are shown in FIG. 4. During the vaginal administration of metronidazole, a positive control currently used as a therapeutic agent for vaginitis disease, there was no change in the community structure observed in the treatment group of *Lactobacillus* strains.

In addition to confirming that the microbial community structure in the vagina, significantly changed taxon profile was analyzed by LefSe program after administration of *Lactobacillus* strains to *Gardnerella vaginalis*-infected mouse.

The results are as shown in cladogram of FIG. 5. From the above analysis, it was confirmed that *Gardnerella vaginalis* and *Staphylococcus* spp. were significantly increased in group (C) infected with *Gardnerella* alone, and the *Lactobacillus* strains were significantly increased in groups (D, E, G) in which the *Lactobacillus* strains of the present invention were administered once after infection with *Gardnerella vaginalis*, thereby the administration of *Lactobacillus* strains changed the vaginal community structure and taxa profile and had a modulatory effect on the vaginal microflora.

The invention claimed is:

1. A method for treating vaginitis comprising administering a *Lactobacillus* sp. to a subject in need,
   wherein the *Lactobacillus* sp. is at least one selected from the group consisting of *Lactobacillus crispatus* SNUV 220 deposited under accession No. KCTC18374P, *Lactobacillus fermentum* SNUV 175 deposited under accession No. KCTC18371P, *Lactobacillus jensenii* SNUV 360 deposited under accession No. KCTC18372P, and *Lactobacillus gasseri* SNUV 281 deposited under accession No. KCTC18375P; and
   wherein the vaginitis is caused by at least one pathogenic vaginal microorganism selected from the group consisting of a *Candida* sp., a *Sneathia* spp., a *Gardnerella* sp., and human papillomavirus.

2. The method of claim 1, wherein
   the *Sneathia* spp. is *Sneathia amnii* or *Sneathia sanguinegens*;
   the *Candida* sp. is *Candida albicans*; or
   the *Gardnerella* sp. strain is *Gardnerella vaginalis*.

3. The method of claim 1, wherein the *Lactobacillus crispatus* SNUV 220 deposited under accession No. KCTC18374P *Lactobacillus fermentum* SNUV 175 deposited under accession No. KCTC18371P, *Lactobacillus jensenii* SNUV 360 deposited under accession No. KCTC18372P, or *Lactobacillus gasseri* SNUV 281 deposited under accession No. KCTC18375P has a survival rate of 50% or higher at a concentration of 0.1% (w/v) bile salt.

4. The method of claim 1, wherein the *Lactobacillus crispatus* SNUV 220 deposited under accession No. KCTC18374P *Lactobacillus fermentum* SNUV 175 deposited under accession No. KCTC18371P, *Lactobacillus jensenii* SNUV 360 deposited under accession No. KCTC18372P, or *Lactobacillus gasseri* SNUV 281 deposited under accession No. KCTC18375P has an activity to inhibit the growth of at least one pathogenic vaginal microorganism selected from the group consisting of a *Candida* sp., a *Sneathia* spp., a *Gardnerella* sp., and human papillomavirus.

5. The method of claim 1, wherein the *Lactobacillus crispatus* SNUV 220 deposited under accession No. KCTC18374P, *Lactobacillus fermentum* SNUV 175 deposited under accession No. KCTC18371P, *Lactobacillus jensenii* SNUV 360 deposited under accession No. KCTC18372P, or *Lactobacillus gasseri* SNUV 281 deposited under accession No. KCTC18375P is administered by oral, transdermal, intravenous, intramuscular, or subcutaneous routes.

* * * * *